(12) United States Patent
Klauber et al.

(10) Patent No.: US 10,093,607 B2
(45) Date of Patent: Oct. 9, 2018

(54) SELECTIVE HYDROLYSIS AND ALCOHOLYSIS OF CHLORINATED BENZENES

(71) Applicant: BASF SE, Ludwigshafen (DE)

(72) Inventors: Eric George Klauber, Bad Duerkheim (DE); Michael Rack, Eppelheim (DE); Thomas Zierke, Hassloch (DE); Nicole Holub, Mannheim (DE); David Cortes, Quincy, IL (US); Gerald Schmelebeck, Buna, TX (US); Junmin Ji, Beaumont, TX (US)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/026,878

(22) PCT Filed: Oct. 2, 2014

(86) PCT No.: PCT/EP2014/071210
§ 371 (c)(1),
(2) Date: Apr. 1, 2016

(87) PCT Pub. No.: WO2015/049360
PCT Pub. Date: Apr. 9, 2015

(65) Prior Publication Data
US 2016/0289157 A1    Oct. 6, 2016

Related U.S. Application Data

(60) Provisional application No. 61/886,679, filed on Oct. 4, 2013.

(30) Foreign Application Priority Data

Oct. 25, 2013 (EP) .................................. 13190194

(51) Int. Cl.
| | | |
|---|---|---|
| C07C 69/76 | (2006.01) |
| C07C 51/377 | (2006.01) |
| C07C 37/02 | (2006.01) |
| C07C 41/16 | (2006.01) |
| C07C 67/297 | (2006.01) |
| C07F 1/00 | (2006.01) |
| C07F 1/04 | (2006.01) |

(52) U.S. Cl.
CPC ............ C07C 51/377 (2013.01); C07C 37/02 (2013.01); C07C 41/16 (2013.01); C07C 67/297 (2013.01); C07F 1/005 (2013.01); C07F 1/04 (2013.01)

(58) Field of Classification Search
CPC ..... C07C 51/377; C07C 67/297; C07C 37/02; C07C 41/16; C07C 39/30; C07C 43/225; C07F 1/005; C07F 1/04
See application file for complete search history.

(56) References Cited

U.S. PATENT DOCUMENTS

| 2,799,714 | A | 7/1957 | Widiger, Jr. et al. |
| 3,013,054 | A * | 12/1961 | Richter .................... C07C 45/54 544/107 |
| 3,399,034 | A | 8/1968 | Genas |
| 3,726,929 | A | 4/1973 | Payne et al. |
| 4,005,151 | A | 1/1977 | Wataya et al. |
| 4,094,913 | A | 6/1978 | Carlson |
| 4,161,611 | A | 7/1979 | Kim |
| 4,232,172 | A | 11/1980 | Becher et al. |

FOREIGN PATENT DOCUMENTS

| CN | 102125035 | 7/2011 |
| CN | 102295552 | 12/2011 |
| CN | 102516072 | 6/2012 |

(Continued)

OTHER PUBLICATIONS 715 (JP 11 049715 published 1999 translated).*

(Continued)

*Primary Examiner* — Yevgeny Valenrod
*Assistant Examiner* — Blaine G Doletski
(74) *Attorney, Agent, or Firm* — Brinks Gilson & Lione

(57) ABSTRACT

The present invention relates to a process for providing a compound of formula (I):

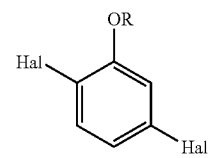

wherein R is hydrogen or R', wherein R' is —(C$_1$-C$_4$)alkyl, and Hal is a halogen, the process comprising the step of:
reacting a compound of formula (II)

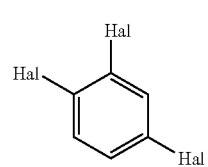

wherein Hal is defined as above,
with an alkali metal alkoxide of the formula XOR', wherein X is an alkali metal, and R' is defined as above.

22 Claims, No Drawings

(56) References Cited

FOREIGN PATENT DOCUMENTS

| | | |
|---|---|---|
| CN | 102838457 | 12/2012 |
| DE | 2509407 | 9/1975 |
| DE | 3512877 | 11/1986 |
| GB | 1 404 435 | 8/1975 |
| JP | 11 49715 | * 2/1999 |
| WO | WO 2001/83417 | 11/2001 |
| WO | WO 2015049160 | 4/2014 |
| WO | WO 2015049360 | 4/2014 |
| WO | WO 2015067494 | 5/2015 |
| WO | WO 2015/095284 | 6/2015 |
| WO | WO 2015082415 | 6/2015 |
| WO | WO 2015082422 | 6/2015 |
| WO | WO 2015086698 | 6/2015 |
| WO | WO 2015124651 | 8/2015 |
| WO | WO 2015/177093 | 11/2015 |

OTHER PUBLICATIONS

Hashimoto et al. (Hydrolysis of 1,2,4-Trichlorobenzene, the Doshisha Enginering Review, vol. 8, No. 2, Aug. 1957.*

Hashimoto et al. translated 1957.*

MCBP (Methoxide Catalysts in Biodiesel Production, pp. 1-3, published 2012).*

Holleman, M.A.F., "Les trois trichorobenzenes et leur reaction avea le methylate de sodium", Recueil des travaux chimiques des pays-bas et de la belique, 1918, p. 195-204, vol. 37 (Year: 1918).*

Decrauw, TH. "The principle of induced alternating polarity in connection with the reacions of derivatives of p-dichlorobenzene and other compounds with sodium methylate", Recueil des travaux chimiques des pays-Bas, Elsevier science Publishes. Amerdam, NL, Jan. 1, 1931, vol. 50, p. 753-792.

Ouellet, S. et al., "Regioselective SNAr reactions of substituted diflourobenzene derivatives: practical synthesis of fluoroaryl ethers and substituted resorcinols", Tetrahedron Letters, Jul. 8, 2009, p. 3776-3779, vol. 50, No. 27.

International Preliminary Report on Patentability dated Apr. 5, 2016, prepared in International Application No. PCT/EP2014/071210.

International Search Report dated Jan. 5, 2015, prepared in International Application No. PCT/EP2014/071210.

Extended European search Report dated Apr. 14, 2014 in European Patent Application No. 13190194.4.

Holleman, M.A.F., "Les trois trichorobenzenes et leur reaction avea le methylate de sodium", Recueil des travaux chimiques des pays-bas et de la belique, 1918, p. 195-204, vol. 37.

Testaferri, L., et al., "The reactions of unactivated aryl halides with sodium methoxide in HPMA", Tetrahedron, 1983, p. 193-197, vol. 29, No. 1.

Kraay, G.M. "L'action du methylate de sodium sur quelques derivres de l'orthodichlorobenzene" Recueil des travaux chimiques des pays-bas, Elsevier Science Publishers, Jan. 1931, p. 753-792, vol. 50.

Smith, M.S. et al., "March's Advanced Organic Chemistry" $5^{th}$ Edition, 2001, p. 860-861, John Wiley & Sons, Inc., New York, USA.

Finger et al., "Aromatic Fluorine Compounds. VIII. Plant Growth Regulators and Intermediates," Journal of the American Chemical Society, vol. 81, (1959), pp. 94-101.

Lin, et al. Synthesis of chlorinated and non-chlorinated biphenyl-2,3- and 3,4-catechols and their [$^2H_3$]-isotopomers, Organic & Biomolecular Chemistry,, 2004, p. 2624-2629, vol. 2, No. 18.

Li et al., "Preparation of Monofluorophenols via the Reaction of Difluorobenzene Derivatives with Potassium Trimethylsilanoate," SynLett, vol. 2009, No. 4, (2009), pp. 633-637.

Noelting et al., "Zur Kenntniss des Amido-p-dichlorbenzols," Berichte der Deutschen Chemischen Gesellschaft, (1905), p. 3506.

Shan et al., "Pd-Catalyzed C—H Oxygenation with TFA/TFAA: Expedient Access to Oxygen-Containing Heterocycles and Late-Stage Drug Modification," Angew. Chem. Int. Ed., vol. 51, (2012), pp. 13070-13074.

Verloop et al., "Use of Linear Free Energy Related and Other Parameters in the Study of Fungicidal Selectivity," Pesticide Science, vol. 7, No. 4, (1976), pp. 379-390.

Li et al., "Pd(OAc)2-Catalyzed Alkoxylation of Arylnitliles via sp2 C—H Bond Activation Using Cyano as the Directing Group," The Journal of Organic Chemistry, vol. 77, No. 18, (2012), pp. 8362-8366.

Zhang et al., "Pd(II)-Catalyzed Hydroxylation of Arenes with 1 atm of O2 or Air," Journal of the American Chemical Society, vol. 131, No. 41, (2009), pp. 14654-14655.

Cresp et al., "Synthesis of Piloquinone, a Metabolite of Streptomyces Pilosus Ettlinger," Journal of the Chemical Society, 1974, pp. 2435-2447.

Schmitz et al., "Ortho-Specific Bromination of Phenols," Journal für praktische Chemie, 1985, vol. 327, No. 6, pp. 998-1006.

Office Action dated Jul. 26, 2017 in U.S. Appl. No. 15/311,951, filed Nov. 17, 2017.

Office Action dated Oct. 24, 2017 in U.S. Appl. No. 15/102,353, filed Jun. 7, 2016.

* cited by examiner

SELECTIVE HYDROLYSIS AND ALCOHOLYSIS OF CHLORINATED BENZENES

This application is a National Stage application of International Application No. PCT/EP2014/071210 filed Oct. 2, 2014, which claims the benefit of U.S. Provisional Application No. 61/886,679, filed Oct. 4, 2013. This application also claims priority under 35 U.S.C. § 119 to European Patent Application No. 13190194.4, filed Oct. 25, 2013.

FIELD OF THE INVENTION

The present invention relates to a process for hydrolyzing 1,2,4-trihalobenzene with improved yield and/or regioselectivity. In a preferred embodiment, the present invention provides an improved process for hydrolyzing 1,2,4-trichlorobenzene for obtaining 2,5-dichlorophenol, which is an important intermediate in the production of the herbicide dicamba (3,6-dichloro-2-methoxybenzoic acid).

BACKGROUND OF THE INVENTION

Dicamba is a selective herbicide currently used for treating e.g. corn, wheat or grassland. It kills broadleaf weeds before and after they sprout. The trivial name dicamba refers to the compound 3,6-dichloro-2-methoxybenzoic acid. The estimated global demand for dicamba in 2012 was about 12.000 metric tons per year. However, it is expected that the global demand for dicamba will increase significantly.

Dicamba is typically produced on an industrial scale from 2,5-dichlorophenol using carboxylation under Kolbe-Schmitt conditions, methylation and subsequently saponification/acidification. 2,5-Dichrophenol in turn can be obtained from 1,4-dichlorobenzene or 1,2,4-trichlorobenzene. The synthetic route via 1,4-dichlorobenzene involves nitration and subsequent diazotation, and, therefore is undesired for use on an industrial scale. The synthetic route via 1,2,4-trichlorobenzene suffers from limited availability of this starting material and from the formation of several byproducts which are formed in the synthesis of 2,5-dichlorophenol.

In order to meet the increasing market demand for compounds such as dicamba, there is a need in the art for processes providing improved yield and/or regioselectivity in the hydrolyzation of 1,2,4-trihalobenzene, such as 1,2,4-trichlorobenzene, so that the limited resources of these compounds can be used more efficiently.

In view of the above, there is further a need in the art for a process for obtaining 2,5-dihalogen substituted phenols, such as 2,5-dichlorophenol, with improved yield and/or regioselectivity. Moreover, there is a particular need in the art for processes and reaction sequences for obtaining dihalogen substituted salicylic acid derivatives, especially including dicamba, in improved yields.

A further object of the present invention is to provide reaction conditions allowing an improved regioselectivity and/or yield in the hydrolyzation of 1,2,4-trihalobenzene for obtaining dihalogen substituted phenols or ultimately dihalogen substituted salicylic acid derivatives, including dicamba. Another object of the present invention is the provision of an improved process for providing 2,5-dichlorophenol. It is a further object of the present invention to implement the improved process for the synthesis of dicamba on an industrial scale. It is another object of the present invention to obtain 2,5-dihalophenol in improved yield. Moreover, since 2,5-dihalophenol alkyl ether can easily be transferred to the corresponding 2,5-dihalophenol, it is a further or alternative object of the present invention to obtain an increased 2,5-regioselectivity.

The object of the present invention is to meet the above needs. In this context it should be noted that even minor improvements in the yield and/or 2,5-regioselectivity in reaction sequences for obtaining dicamba would provide a tremendous benefit. For example, an improvement of yield and/or 2,5-regioselectivity of 1% would provide an additional annual amount 120 metric tons of dicamba.

SUMMARY OF THE INVENTION

The present invention relates to an improved process for hydrolyzing 1,2,4-trihalobenzene to obtain a compound of formula (I):

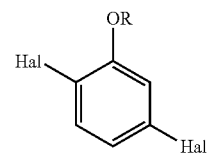

wherein R is hydrogen or R', wherein R' is —$(C_1$-$C_4)$alkyl, and Hal is a halogen atom.

In particular, the present invention is directed to a process for providing the above compound of formula (I), comprising the step of: Reacting a compound of formula (II)

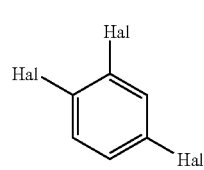

wherein Hal is defined as above, with an alkali metal alkoxide of the formula XOR', wherein X is an alkali metal, and R' is defined as above.

In a preferred embodiment, the above process is carried out in a solvent, wherein the solvent is an alcohol of formula HOR', wherein R' is as defined above.

Conventional processes for hydrolyzing 1,2,4-trihalobenzene are typically carried out using an alkali metal hydroxide such as NaOH, and an alcoholic solvent such as methanol. The reaction results in a mixture of different regioisomers, i.e. 2,5-regioisomers, 2,4-regioisomers, and 3,4-regioisomers, and derivatives as defined in further detail below.

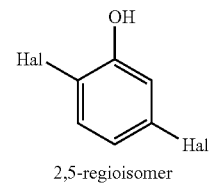

2,5-regioisomer

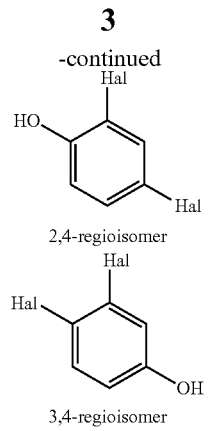

2,4-regioisomer 3,4-regioisomer

For example, hydrolyzing 1,2,4-trichlorobenzene in methanol using NaOH results in a mixture of 2,5-dichlorophenol, 2,4-dichlorophenol, 3,4-dichlorophenol, 2,5-dichlorophenol methyl ether, 2,4-dichlorophenol methyl ether, and 3,4-dichlorophenol methyl ether. In view of the high commercial importance of 2,5-dichlorophenol, even minor improvements in the yield thereof in the reaction would provide a tremendous benefit for the overall yield of the final product, i.e. dicamba. Moreover, since 2,5-dichlorophenol methyl ether in principle can be further reacted to obtain 2,5-dichlorophenol, processes resulting in an improved 2,5-regioselectivity (i.e. hydrolyzation in the 2-position of 1,2,4-trichlorobenzene) are also highly desirable.

The present inventors have found that by using alkali metal alkoxide for the hydrolysis reaction of 1,2,4-trihalobenzene instead of alkali metal hydroxide the yield of 2,5-dihalophenol can be improved. The present inventors also found that the 2,5-regioslectivity can be improved by employing alkali metal alkoxide instead of alkali metal hydroxide.

In a preferred embodiment, the alkali metal alkoxide of formula XOR' is added to the reaction mixture in the form of an alcoholic solution in an alcohol of formula HOR', wherein X and R' are as defined above. In a further preferred embodiment, the concentration of the alcoholic alkali metal alkoxide solution added to the reaction mixture is about 20 wt.-% to about 67 wt.-%, based on the total weight of the alcohol HOR' and the alkali metal alkoxide XOR'. In a more preferred embodiment, the concentration of the alcoholic alkali metal alkoxide solution added to the reaction mixture is about 25 wt.-% to about 67 wt.-%.

In another preferred embodiment of the present invention, about one molar equivalent of the compound of formula (II) is reacted in the presence of about 2 to about 3 molar equivalents of the alkali metal alkoxide of formula XOR' in about 2 to about 14 molar equivalents of a solvent of formula HOR'. In another more preferred embodiment, about one molar equivalent of the compound of formula (II) is reacted in the presence of about 2.2 to about 2.6 molar equivalents of the alkali metal alkoxide of formula XOR' in about 11.5 to about 12.5 molar equivalents of a solvent of formula HOR'. Furthermore, in still more preferred embodiments, about one molar equivalent of the compound of formula (II) is reacted in the presence of about 2.4 molar equivalents of the alkali metal alkoxide of formula XOR' in about 12 molar equivalents of a solvent of formula HOR'.

The step of reacting the compound of formula (II) with an alkali metal alkoxide of formula XOR' is preferably carried out at a temperature of at least 150° C. More preferably the step of reacting the compound of formula (II) with the alkali metal alkoxide is carried out at a temperature of 150° C. to about 190° C. In one preferred embodiment, the reaction is carried out at a temperature of about 150° C. to about 170° C. In another preferred embodiment, the reaction is carried out at a temperature of about 170° C. to about 190° C.

As regards the reaction time, it is preferred that the step of reacting the compound of formula (II) with an alkali metal alkoxide of formula XOR' is carried out within 30 to 180 minutes. In a more preferred embodiment, the reaction is carried out within 45 to 120 minutes, such as 90 minutes.

In a preferred embodiment, the present invention relates to a process as defined above providing the compound of formula (I) in a 2,5-regioselectivity of at least 72%. More preferably, the compound of formula (I) is obtained in a 2,5-regioselectivity of at least 74%, still more preferably of at least 75%, even more preferably of at least 76%, and most preferably of at least 77%.

The hydrolyzation product of compounds of formula (I) according to the present invention represents a valuable product or intermediate for chemical synthesis. Thus, the hydrolyzation product of formula (I) can be further reacted to obtain other valuable chemicals or intermediates. In a preferred embodiment of the present invention the compound of formula (I) is reacted to obtain a compound of formula (III)

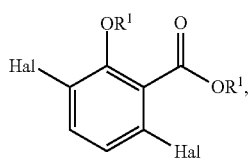

III wherein Hal is as defined above, and $R^1$ is an alkali metal.

The above reaction from compounds of formula (I) to compounds of formula (III) is known in the art as the "Kolbe-Schmitt reaction". Reactions under Kolbe-Schmitt conditions can be carried out on an industrial scale in good yields. For example, the above conversion is part of known reaction sequences for obtaining dicamba from 2,5-dichlorophenol. The reaction is typically carried out in the presence of an alkali metal hydroxide and carbon dioxide.

In a further preferred embodiment, the compound of formula (III) is used to obtain a compound of formula (IV)

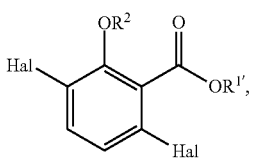

IV wherein $R^2$ is —$(C_1-C_4)$alkyl, $R^{1'}$ is an alkali metal or is the same as $R^2$, and Hal is as defined above. This reaction step is also carried out in prior art reaction sequences for obtaining dicamba. In these preferred embodiments, the carboxylic group may partly be converted to the corresponding ester and partly remains in deprotonated from. Since dicamba, which exhibits a free carboxylic acid group, is a preferred reaction product according to the present invention, it is not relevant in this reaction step that the carboxylic acid group is only partly converted. Rather, final end products containing a free carboxylic acid group can be obtained in subsequent reaction steps.

For example, in a further preferred embodiment according to the invention, the resulting product of formula (IV) is converted to the corresponding carboxylic acid by hydrolyzing an ester of formula (IV) (i.e. wherein $R^{1'}$ is —($C_1$-$C_4$)alkyl) under basic conditions, and is subsequently acidified to obtain a compound of formula (V)

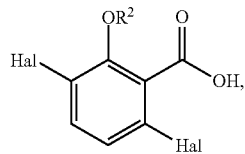

V wherein $R^2$ and Hal are as defined above.

The above reaction step can be carried out analogously to prior art reactions sequences for obtaining dicamba from 2,5-dichlorophenol in good yields on an industrial scale.

In further especially preferred embodiments, R is selected from hydrogen and R'; and R' is selected from methyl and ethyl. More preferably, R' is methyl. In the reaction step for obtaining the compound of formula (I) according to the present invention, typically a mixture of phenol derivatives, in which R is hydrogen, and the corresponding phenol alkyl ether derivatives, in which R is R', are obtained. In principle, phenol alkyl ether derivatives can be further reacted to the corresponding phenol derivatives as described in further detail below.

In especially preferred embodiments according to the invention, X is sodium or potassium. More preferably, X is sodium. Thus, the alkali metal alkoxide of formula XOR' used for the hydrolyzation reaction for obtaining the compound of formula (I) is preferably a potassium alkoxide or sodium alkoxide, such as sodium methoxide.

In preferred embodiments, $R^1$ is selected from sodium and potassium. $R^1$ is derived from an alkali metal hydroxide, i.e. sodium hydroxide or potassium hydroxide used during the Kolbe-Schmitt reaction step. It may further be advantageous to replace one alkali metal with another alkali metal in preferred embodiments of the invention as described below. In a preferred embodiment, $R^1$ is potassium in the above-described Kolbe-Schmitt reaction step, i.e. KOH is used in the step of providing the compound of formula (III).

In further preferred embodiments according to the present invention, in case $R^{1'}$ is not an alkali metal in the compound of formula (IV) described above, $R^{1'}$ is ethyl or methyl. In these cases, $R^{1'}$ is identical to $R^2$. $R^2$ is, according to preferred embodiments, also selected from ethyl and methyl. In a more preferred embodiment, $R^2$ is methyl, thus also $R^{1'}$ is more preferably methyl in case it is not an alkali metal. In case $R^{1'}$ is an alkali metal, it may be identical to $R^1$ as defined above, or preferably is an alkali metal different from $R^1$, i.e. can be different in different reaction steps. For example, $R^{1'}$ may be Na or may be identical to $R^2$.

In especially preferred embodiments, the processes according to the present invention are employed for obtaining dicamba. In these preferred embodiments, the compound of formula (V) is

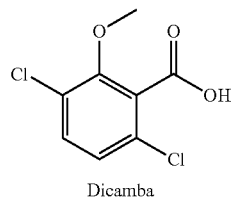

Dicamba

Further preferred embodiments of the present invention are apparent from the following detailed description and the attached claim set.

DETAILED DESCRIPTION OF THE INVENTION

In the following, illustrative embodiments of the present invention are described in more detail.

The term "Hal" or "halogen" as used herein refers to a halogen atom independently selected from F, Cl, Br and I. More preferably, Hal is independently selected from Cl and Br. In still further preferred embodiments both substituents Hal are identical and most preferably are Cl.

The term "alcoholic solution" as used refers to a solution of a chemical compound in an alcohol, in particular, an alcohol of formula HOR', wherein R' is as defined above. The term "alcoholic alkali metal alkoxide solution" refers to the solution of an alkali metal alkoxide in an alcohol, especially a solution of an alkali metal alkoxide of formula XOR' in an alcohol of formula HOR', wherein X and R' are as defined above.

The present invention relates to an improved process for hydrolyzing a compound of formula (II) to obtain a corresponding phenol or phenol alkyl ether of formula (I) with improved yield and/or regioselectivity. According to industrial processes in the prior art, hydrolyzation of 1,2,4-trihalobenzenes, such as 1,2,4-trichlorobenzene, is carried out using NaOH in an alcoholic solvent. For example, hydrolyzation of 1,2,4-trichlorobenzene with NaOH in methanol affords 2,5-dichlorophenol in a yield of 64.6%. Furthermore, in this reaction several byproducts are obtained, namely 2,5-dichlorophenol methyl ether, 2,4-dichlorophenol methyl ether, 3,4-dichlorophenol methyl ether, 2,4-dichlorophenol, and 3,4-dichlorophenol. The 2,5-regioselectivity obtained in the above reaction according to the prior art is 71.9%.

The term "2,5-regioselectivity" refers to the ratio of the combined amount(s) of 2,5-dihalophenol and 2,5-dihalophenol alkyl ether to the total amount of 2,5-dihalophenol, 2,5-dihalophenol alkyl ether, 2,4-dihalophenol, 2,4-dihalophenol alkyl ether, 3,4-dihalophenol, and 3,4-dihalophenol alkyl ether obtained in the reaction. For example, the term "2,5-regioselectivity" employed above in connection with prior art processes for obtaining 2,5-dichlorophenol from 1,2,4-trichlorobenzene using NaOH in methanol refers to the combined amounts of 2,5-dichlorophenol and 2,5-dichlorophenol methyl ether to the total amount of 2,5-dichlorophenol, 2,5-dichlorophenol methyl ether, 2,4-dichlorophenol, 2,4-dichlorophenol methyl ether, 3,4-dichlorophenol, and 3,4-dichlorophenol methyl ether obtained.

Analogously, the term "2,4-regioselcetivity" refers to the ratio of the combined amount(s) of 2,4-dihalophenol and 2,4-dihalophenol alkyl ether to the total amount of 2,5-dihalophenol, 2,5-dihalophenol alkyl ether, 2,4-dihalophenol, 2,4-dihalophenol alkyl ether, 3,4-dihalophenol, and 3,4-dihalophenol alkyl ether obtained.

In addition, the term "3,4-regioselectivity" refers to ratio of the combined amount(s) of 3,4-dihalophenol and 3,4-dihalophenol alkyl ether to the total amount of 2,5-dihalophenol, 2,5-dihalophenol alkyl ether, 2,4-dihalophenol, 2,4-dihalophenol alkyl ether, 3,4-dihalophenol, and 3,4-dihalophenol alkyl ether obtained.

In the context of the present invention it is desired to reduce the degree of 2,4-regioselectivity and 3,4-regioselectivity, since the corresponding compounds cannot be converted to the preferred products of formula (V). A preferred product obtained in the processes according to the invention is 2,5-dichlorophenol used in the production of dicamba.

The term "alkali metal" when used in the context of the present invention refers to lithium, sodium or potassium. Sodium and potassium are preferred.

The present inventors have found that the use an alkali metal alkoxide instead of an alkali metal hydroxide in the above hydrolysis provides better yields of 2,5-dihalophenol, such as 2,5-dichlorophenol, and/or improved 2,5-regioselectivity. The present inventors have further found specific preferred reaction conditions for further improving the yield of the desired compounds and/or the desired 2,5-regioselectivity.

Thus, the present invention relates to an improved process for hydrolyzing 1,2,4-trihalobenzene of formula (II) to obtain a compound of formula (I):

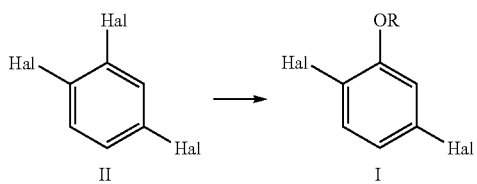

wherein R is hydrogen or R', wherein R' is —$(C_1$-$C_4)$alkyl, and Hal is a halogen, in the presence of an alkali metal alkoxide of the formula XOR', wherein X is an alkali metal, and R' is defined as above. The process may be carried out in a solvent, wherein the solvent is an alcohol of formula HOR', wherein R' is as defined above. As shown in the below working examples, the use of an alkali metal alkoxide instead of an alkali metal hydroxide results in improved yields and/or improved 2,5-regioselectivity.

The reaction is typically carried out in a pressure reactor. The solvent and the reactants are added to the pressure reactor, the pressure reactor is sealed and subsequently heated to the desired reaction temperature under agitation. After the desired reaction time, the pressure reactor is cooled to room temperature. The product can be isolated by transferring the reaction mixture into a separation device, such as a separation funnel, acidifying the mixture using a suitable acid such a $H_2SO_4$ or HCl to a pH of e.g. less than 1.5, and extracting the mixture using a suitable organic solvent, such as an ether (e.g. methyl tert.-butyl ether) or methylene chloride ($CH_2Cl_2$). Continuous extraction in a suitable device or sequential extraction (e.g. three times) can be employed.

It is preferred according to the present invention that the alkali metal alkoxide of formula XOR' is added to the reaction mixture in the form of an alcoholic solution in an alcohol of formula HOR', wherein X and R' are as defined above. The present inventors have found that the concentration of the alcoholic alkali metal alkoxide solution added to the reaction mixture has an influence on the yields obtained and/or 2,5-regioselectivity. Therefore, the concentration of the alcoholic alkali metal alkoxide solution added to the reaction mixture is preferably about 20 wt.-% to about 67 wt.-%, based on the total weight of alcohol and alkali metal alkoxide. In more preferred embodiments, the concentration of the alcoholic alkali metal alkoxide solution added to the reaction mixture is about 25 wt.-% to about 67 wt.-%.

The reaction temperature is preferably at least 150° C., such as 150° C. to about 190° C. In one preferred embodiment, the reaction is carried out at a temperature of about 150° C. to about 170° C. In another preferred embodiment, the reaction is carried out at a temperature of about 170° C. to about 190° C.

The reaction is preferably carried out within 30 to 180 minutes. In a more preferred embodiment, the reaction is carried out within 45 to 120 minutes, such as 90 minutes.

The present inventors have found that under specific reaction conditions including reaction temperature, concentration of the alcoholic alkali metal alkoxide solution, and reaction time, the yield of the compound of formula (I) can be further improved. Thus, in case the yield of the compound of formula (I) should be optimized, the reaction is preferably carried out at relatively high reaction temperatures for a moderate reaction time using a relatively low concentration of the alcoholic alkali metal alkoxide solution. In a preferred embodiment, the yield of the compound of formula (I) is optimized by carrying out the reaction at a temperature of about 180° C. to about 190° C. for a reaction time of about 80 to about 100 minutes using concentration of the alcoholic alkali metal alkoxide solution of about 20 wt.-% to about 30 wt.-%.

In alternative cases, when the 2,5-regioselectivity is the main focus for optimization, it is preferred to carry out the reaction at moderate reaction temperatures for a moderate reaction time using a high concentration of the alcoholic alkali metal alkoxide solution. In a preferred embodiment, the 2,5-regioselectivity is optimized by carrying out the reaction at a temperature of about 150° C. to about 170° C. for a reaction time of about 80 to about 100 minutes using concentration of the alcoholic alkali metal alkoxide solution of about 50 wt.-% to about 67 wt.-%.

Compounds of formula (I) in which R is R' can be hydrolyzed under basic conditions to compounds of formula (I) in which R is hydrogen. Suitable bases include e.g. alkali metal hydroxides such as NaOH or KOH. The conversion can be carried out in a suitable organic solvent such as an alcohol. The obtained alkali metal salts can be subsequently acidified with acid such as $H_2SO_4$ or HCl to give compound of formula (I) in which R is hydrogen.

In a further preferred embodiment, the compound of formula (I), in which R is hydrogen, is converted into valuable chemical products or intermediates. In an especially preferred embodiment, the compound of formula (I), in which R is hydrogen, is subjected to a carboxylation reaction under Kolbe-Schmitt conditions to obtain a compound of formula (III).

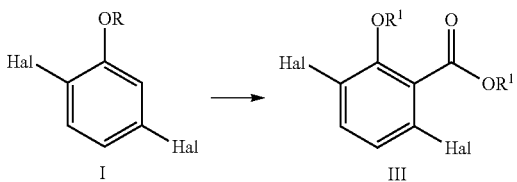

In the carboxylation step, the compound of formula (I) is first converted into the corresponding phenolate by treating with an alkali metal hydroxide R¹OH. For example, sodium hydroxide or potassium hydroxide is employed here, whereof potassium hydroxide is preferred. The alkali metal hydroxide is used in about stoichiometric amounts in an aqueous solution having e.g. a concentration of 50 wt.-%. The conversion can be carried out in a suitable organic solvent such as e.g. xylene. Water can be removed from the system using azeotropic distillation.

Subsequently, the phenolate is contacted with gaseous $CO_2$ under high pressure. The phenolate solution in e.g. xylene can be used without further workup. The reaction affords the carboxylic acid salt of formula (III), which normally is not soluble in the reaction medium such as toluene and, therefore, can easily be separated.

In a further preferred embodiment, the compound of formula (III) is alkylated to obtain a compound of formula (IV).

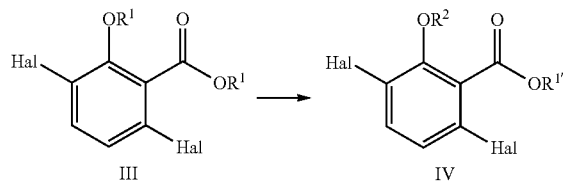

The reaction is accomplished by reacting the compound of formula (III) with an alkyl halide of formula $YR^2$, wherein Y is halogen, such as Cl, Br or I, preferably Cl or Br, more preferably Cl. In a preferred embodiment, the alkyl halide is methyl chloride. The reaction can be carried out in aqueous solution. During the reaction, the pH, temperature and pressure may be controlled such that the reaction is carried out at a pH of about 8 to about 12, a temperature of about 90° C. to about 100° C. and a pressure of about 500 to about 1050 kPa. An excess of alkyl halide is normally used. Thus, it is not excluded that the compound of formula (IV) is partly esterified. In these cases, $R^{1'}$ is identical to $R^2$.

Furthermore, in order to increase solubility of the compound of formula (IV), the double salt may be converted in advance of the reaction to a corresponding mixed salt by treating with an alkali metal hydroxide different from the alkali metal hydroxide used in the previous reaction step. For example, when potassium hydroxide is used in the Kolbe-Schmitt reaction step, the compound of formula (IV) may be treated with sodium hydroxide in advance of the alkylation step to obtain a mixed potassium/sodium salt. In these cases, $R^{1'}$ may be an alkali metal different from $R^1$. In other cases, $R^{1'}$ is identical to $R^1$.

In a further preferred embodiment, the compound of formula (IV) is converted to the compound of formula (V).

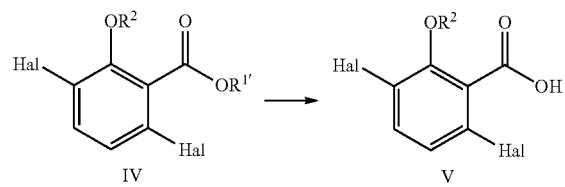

In cases where the compounds of formula (IV) include an ester in which $R^{1'}$ is identical to $R^2$, the ester is hydrolyzed under basic conditions using a suitable base to obtain the corresponding carboxylic acid salts. For example, alkali metal hydroxides such as NaOH may be employed here. Compounds of formula (IV) in which $R^{1'}$ is an alkali metal salt may be present during hydrolysis without harm. Thus, a composition comprising a compound of formula (IV) in which $R^{1'}$ is an alkali metal, such as sodium, is obtained.

The alkali metal salt of formula (IV) is then acidified in solution using a suitable acid, such as $H_2SO_4$ or HCl, preferably HCl, to afford the compound of formula (V). In cases where a compound of formula (IV) in which $R^{1'}$ is an alkali metal is obtained in the previous reaction step, the composition can be directly subjected to acidification without the above hydrolyzation.

Although the processes and preferred processes according to the present invention as described above can be employed for providing a variety of final products and intermediates, the present invention will be illustrated by describing a reaction sequence for obtaining dicamba starting from 1,2,4-trichlorobenzene. A person skilled in the art will comprehend that certain reaction steps in this sequence are preferred as opposed to essential, and will further be able to adapt the processes described herein for the production of other compounds and intermediates within the scope of the appended claims.

In an especially preferred embodiment, the present invention provides a process for obtaining dicamba starting from 1,2,4-trichlorobenzene. In a first step of the reaction sequence, 1,2,4-trichlorobenzene is subjected to a hydrolyzation reaction using sodium methoxide in methanol as described above to obtain 2,5-dichlorophenol with an improved yield and/or 2,5-regioselectivity.

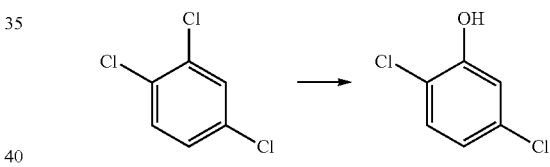

1,2,4-trichlorobenzene is a compound within the definition of formula (II) as defined above, in which Hal is Cl. Furthermore, 2,5-dichlorophenol is a compound within the definition of formula (I) according to the present invention, in which Hal is Cl, and R is H.

According to preferred embodiments of the invention, 2,5-dichlorophenol is further subjected to carboxylation under Kolbe-Schmitt conditions using KOH and $CO_2$ as described above to obtain the dipotassium salt of 3,6-dichlorosalicylic acid.

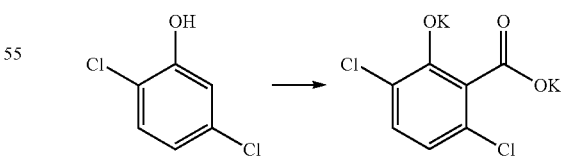

The dipotassium salt of 3,6-dichlorosalicylic acid is a compound according to formula (III) of the present invention, in which Hal is Cl, and $R^1$ is K.

It is further preferred that the dipotassium salt of 3,6-dichlorosalicylic acid is methylated in a subsequent reaction step using methyl chloride. As described above, this conversion may include converting the dipotassium salt into a mixed salt in order to improve solubility in water. In a preferred embodiment, NaOH is used for the provision of the mixed salt. In view of this, methylation of dipotassium 3,6-dichlorosalicylic acid after conversion into a mixed salt affords typically a mixture of the sodium and/or potassium form of 3,6-dichloro-2-methoxybenzoic acid and 3,6-dichloro-2-methoxybenzoic acid methyl ester.

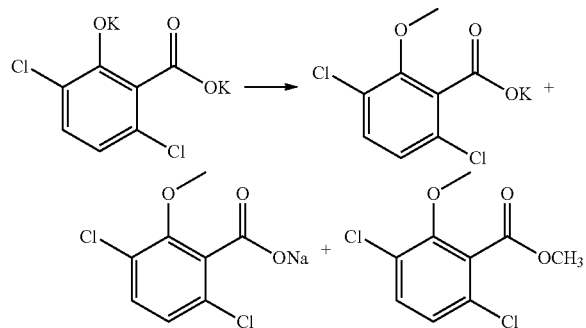

The product obtained in the reaction is a compound according to formula (IV) of the present invention in which Hal is Cl, $R^2$ is methyl, and $R^{1'}$ is either K, Na or methyl.

The above mixture is subsequently preferably converted to dicamba by hydrolyzing the ester compounds in the mixture using NaOH as described above and subsequently acidifying the resulting product using HCl as outlined above.

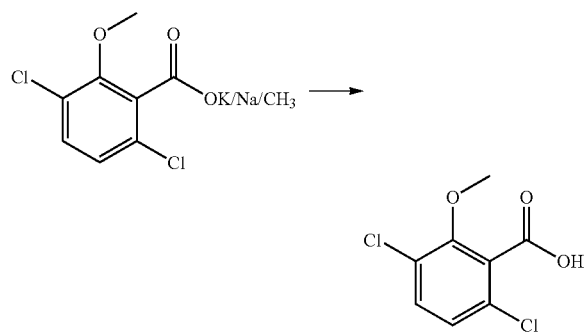

Dicamba is a compound according to formula (V) of the present invention, in which Hal is Cl, and $R^2$ is methyl.

The above reaction sequence can be carried out on an industrial scale. The overall yield of the final products and intermediates is improved over the overall process since the yield and/or desired regioselectivity required is improved in the first process step of the sequence. Thus, in a preferred embodiment, the present invention provides an advantageous synthetic route to dicamba for production on industrial scale with improved yields starting from 1,2,4-trichlorobenzene.

EXAMPLES

The present invention will be further illustrated by means of a comparative example and working examples.

1. Comparative Example 1,2,4-trichlorobenzene (TCB), NaOH (in the form of a 50 wt-% solution in water) and methanol were charged into a pressure reactor. The molar ratio of TCB:NaOH:methanol was 1.0:2.4:10. Afterwards, the pressure reactor was sealed, heated to 190° C. under agitation and held at this temperature for 90 minutes. During the reaction, agitation was continued. The reactor was then cooled to room temperature using an ice-$H_2O$ bath.

The reaction mixture was then transferred into a separation funnel and acidified with 10% $H_2SO_4$ to a pH of below 1.5. The aqueous layer of the resulting two-layer mixture was then extracted three times with methylene chloride.

The obtained yield of 2,5-dichlorophenol and 2,5-dichloroanisole combined was 64.6%. The obtained regioselectivity (2,5-dichlorophenol and 2,5-dichlorophenol methyl ether/2,4-dichlorophenol and 2,4-dichlorophenol methyl ether/3,4-dichlorophenol and 3,4-dichlorophenol methyl ether) was 71.9/15.5/12.6 (analysis using GC).

2. Working Example 1

The above comparative example was repeated except for using a 25% solution of NaOMe in methanol as the base. The molar ratio of TCB:NaOMe:methanol was 1.0:2.4:12. The obtained yield of 2,5-dichlorophenol and 2,5-dichloroanisole combined was 73.9%. The obtained 2,5-regioselectivity was 74.2%.

3. Working Example 2

Working example 1 was repeated except for carrying out the reaction for 45 minutes. The obtained yield of 2,5-dichlorophenol and 2,5-dichloroanisole combined was 72.0%. The obtained 2,5-regioselectivity was 74.5%.

4. Working Example 3

Working example 1 was repeated except for carrying out the reaction at a temperature of 150° C. The obtained 2,5-regioselectivity was 75.4%.

5. Working Example 4

Working example 1 was repeated except for using a 35% solution of NaOMe and carrying out the reaction at a temperature of 170° C. The obtained yield of 2,5-dichlorophenol and 2,5-dichloroanisole combined was 70.6%. The obtained 2,5-regioselectivity was 76.2%.

6. Working Example 5

Working example 1 was repeated except for using a 50% solution of NaOMe and carrying out the reaction at a temperature of 160° C. The obtained 2,5-regioselectivity was 76.8%.

7. Working Example 6

Working example 5 was repeated except for using a 67% solution of NaOMe. The obtained 2,5-regioselectivity was 78.0%.

TABLE 1

Improvement in yield of 2,5-dichlorophenol and 2,5-dichloroanisole combined

| | Combined Yield [%] |
|---|---|
| Comparative Example | 64.6 |
| Working Example 1 | 73.9 |
| Working example 2 | 72.0 |

TABLE 2

Improvement in 2,5-regioselectivity

| | 2,5-regioselectivity [%] |
|---|---|
| Comparative Example | 71.9 |
| Working Example 3 | 75.4 |
| Working Example 4 | 76.2 |
| Working Example 5 | 76.8 |
| Working Example 6 | 78.0 |

The invention claimed is:

1. A process for providing a compound of formula (I):

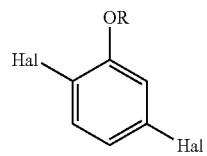

I wherein R is hydrogen or R', wherein R' is $(C_1\text{-}C_4)$alkyl, and Hal is chloro, the process comprising the step of:

reacting a compound of formula (II)

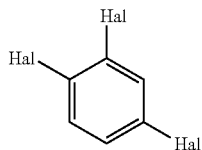

II wherein Hal is defined as above, with an alkali metal alkoxide of the formula XOR', wherein X is an alkali metal, and R' is defined as above, wherein the alkali metal alkoxide of formula XOR' is added to the reaction mixture in the form of an alcoholic solution in an alcohol of formula HOR' having a concentration of 25 wt.-% to 67 wt.-%, based on the weight of the total weight of the alcohol HOR' and the alkali metal alkoxide of the formula XOR'; and wherein the step of reacting the compound of formula (II) with an alkali metal alkoxide of formula XOR' is carried out at a temperature of at least 150° C.

2. The process according to claim 1, wherein the process is carried out in a solvent, wherein the solvent is an alcohol of formula HOR', wherein R' is as defined in claim 1.

3. The process according to claim 1, wherein about one molar equivalent of the compound of formula (II) is reacted in the presence of 2 to 3 molar equivalents of the alkali metal alkoxide of formula XOR' in 2 to 14 molar equivalents of a solvent of formula HOR'.

4. The process according to claim 3, wherein about one molar equivalent of the compound of formula (II) is reacted in the presence of 2.2 to 2.6 molar equivalents of the alkali metal alkoxide of formula XOR' in 11.5 to 12.5 molar equivalents of a solvent of formula HOR'.

5. The process according to claim 4, wherein about one molar equivalent of the compound of formula (II) is reacted in the presence of about 2.4 molar equivalents of the alkali metal alkoxide of formula XOR' in about 12 molar equivalents of a solvent of formula HOR'.

6. The process according to claim 1, wherein the step of reacting the compound of formula (II) with an alkali metal alkoxide of formula XOR' is carried out at 150° C. to 190° C.

7. The process according to claim 1, wherein the step of reacting the compound of formula (II) with an alkali metal alkoxide of formula XOR' is carried out within 30 to 180 minutes.

8. The process according to claim 7, wherein the step of reacting the compound of formula (II) with an alkali metal alkoxide of formula XOR' is carried out within 45 to 120 minutes.

9. The process according to claim 1, wherein the compound of formula (I) is obtained in a 2,5-regioselectivity of at least 72.

10. The process according to claim 9, wherein the compound of formula (I) is obtained in a 2,5-regioselectivity of at least 77%.

11. The process according to claim 1, wherein the compound of formula (I), in which R is hydrogen or $(C_1\text{-}C_4)$ alkyl, is obtained in a yield of at least 70%.

12. The process according to claim 11, wherein the compound of formula (I), in which R is hydrogen or —$(C_1\text{-}C_4)$alkyl, is obtained in a yield of at least 74%.

13. The process according to claim 1, further comprising the step of reacting the compound of formula (I) to obtain a compound of formula (III)

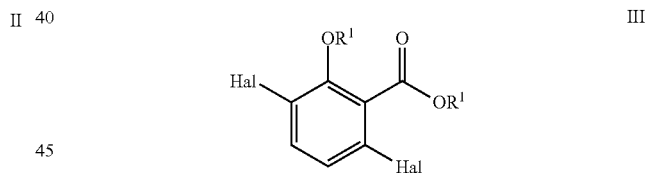

III wherein $R^1$ is an alkali metal.

14. The process according to claim 13, wherein the step of reacting the compound of formula (I) to obtain a compound of formula (III) is carried out in the presence of an alkali metal hydroxide and carbon dioxide.

15. The process according to claim 13, further comprising the step of reacting the compound of formula (III) to obtain a compound of formula (IV)

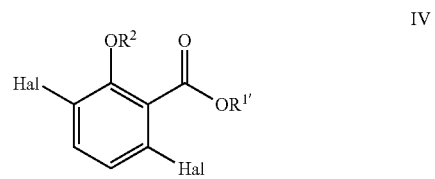

IV wherein $R^2$ is —$(C_1\text{-}C_4)$alkyl, $R^{1'}$ is an alkali metal or is the same as $R^2$.

16. The process according to claim 15, further comprising the step of reacting the compound of formula (IV) to obtain a compound of formula (V)

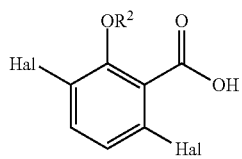

wherein $R^2$ and Hal are as defined in claim 15.

17. The process according to claim 1, wherein
(b) R is selected from hydrogen and R'; and R' is selected from methyl and ethyl; and/or
(c) X is sodium or potassium.

18. The process according to claim 17, wherein
(f) R' is methyl.

19. The process according to claim 17, wherein
(g) X is sodium.

20. The process according to claim 15, wherein
(a) R is selected from hydrogen and R'; and R' is selected from methyl and ethyl; and/or
(b) X is sodium or potassium; and/or
(c) $R^1$ is selected from sodium and potassium; and/or
(d) $R^{1'}$ is selected from sodium and potassium, or $R^{1'}$ is $R^2$, and $R^2$ is selected from ethyl and methyl.

21. The process according to claim 16, wherein the compound of formula (V) is

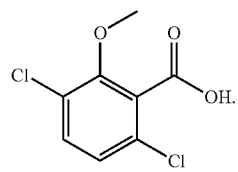

22. The process according to claim 20, wherein
(h) $R^{1'}$ is $R^2$, and $R^2$ is methyl.

* * * * *